United States Patent [19]

Waltz

[11] Patent Number: 5,062,828

[45] Date of Patent: Nov. 5, 1991

[54] HYPODERMIC SYRINGE

[76] Inventor: Roger L. Waltz, 1000 W. 4th #4, Grandview, Wash. 98930

[21] Appl. No.: 475,702

[22] Filed: Feb. 6, 1990

Related U.S. Application Data

[63] Continuation-in-part of Ser. No. 321,999, Mar. 13, 1989, abandoned, which is a continuation of Ser. No. 106, 780, Oct. 8, 1987, abandoned.

[51] Int. Cl.$^5$ ............................................. A61M 5/315
[52] U.S. Cl. ..................................... 604/51; 604/125; 604/218; 73/327
[58] Field of Search ................. 604/51, 122, 124, 125, 604/187, 189, 207, 218, 235, 224; 222/158; 73/327, 427, 429, 864.13, 864.16

[56] References Cited

U.S. PATENT DOCUMENTS

| | | | |
|---|---|---|---|
| 330,621 | 11/1885 | Reichardt | 604/207 |
| 332,920 | 12/1885 | Martin | 73/327 |
| 827,383 | 7/1906 | McElroy et al. | 604/218 |
| 1,136,108 | 4/1915 | Curtis | 222/158 |
| 1,597,608 | 8/1926 | Ligotz | 73/327 |
| 2,283,915 | 5/1942 | Cole | 222/158 |
| 2,303,154 | 11/1942 | Armstrong | 73/327 |
| 2,586,581 | 2/1952 | Tschischeck | 350/116 |
| 2,888,015 | 5/1959 | Hunt | 604/207 |
| 3,512,862 | 5/1970 | Yin | 350/110 |
| 3,690,312 | 9/1972 | Leibinsohn | 73/327 |
| 3,694,090 | 9/1972 | Ohyama | 356/148 |
| 3,727,242 | 4/1973 | Miller | 73/327 |
| 3,774,603 | 11/1973 | McPhee | 73/327 |
| 3,885,562 | 5/1975 | Lampkin | 604/218 |
| 4,178,071 | 12/1979 | Asbell | 350/116 |

FOREIGN PATENT DOCUMENTS 1261 of 1904 United Kingdom ............... 604/218

Primary Examiner—Stephen C. Pellegrino
Assistant Examiner—Ralph A. Lewis
Attorney, Agent, or Firm—Wells, St. John & Roberts

[57] ABSTRACT

A small bore plastic syringe body is disclosed with improved visual amplification of interface surfaces between a light transmissive liquid and air within the syringe bore using a solid reflective colored strip on the syringe tube and located on one side thereof. An assembly including the syringe body provides a plunger and piston received within the tube to define an expansible chamber. The strip is narrower between its side edges than the outer tube diameter, yet is of sufficient width dimension that an image of the strip, when viewed through liquid in the expansible chamber, appears brightly and as wide as the tube. Where air is present in the expansible chamber, a diffused image of the strip will appear through the tube walls that is narrower than the actual strip width dimension. The stark visual contrast between the enlarged colored strip image "filling" the tube with solid bright color and the reduced diffused image with colorless spaces on either side dramatically improves the observer's ability to determine if there is air present within the liquid column in the tube.

1 Claim, 2 Drawing Sheets

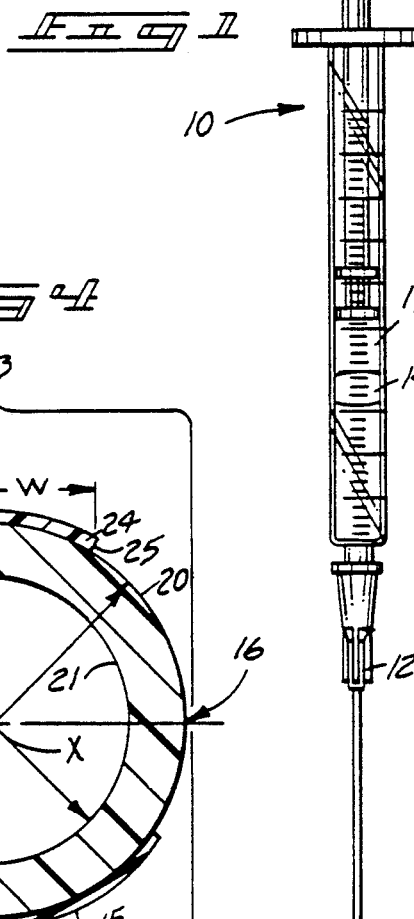
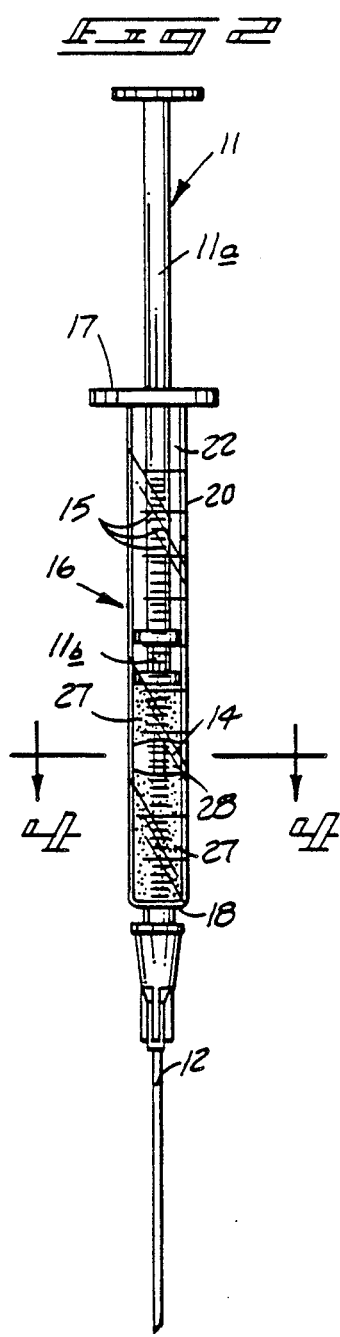
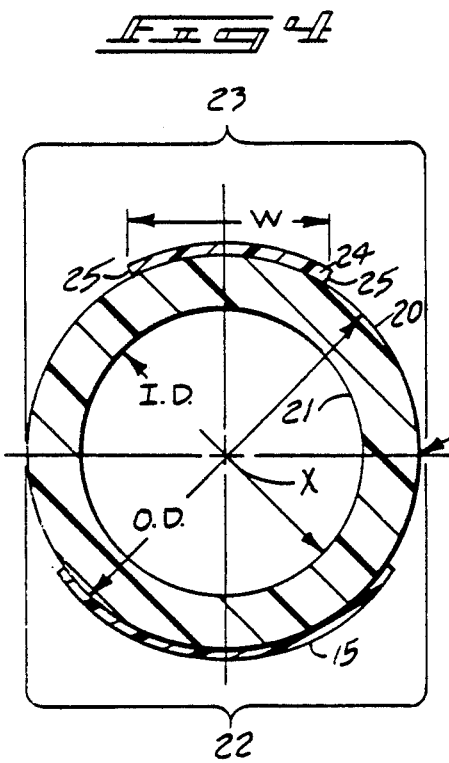
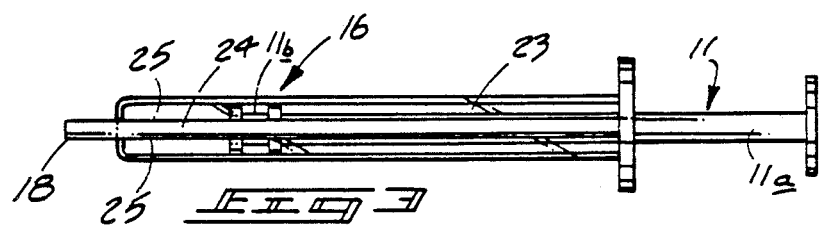

HYPODERMIC SYRINGE

RELATED APPLICATIONS

The present application is a continuation-in-part of co-pending application Ser. No. 321,999, filed Mar. 13, 1989, now abandoned which is a continuation of application Ser. No. 106,780, filed Oct. 8, 1987, now abandoned.

FIELD OF THE INVENTION

The present invention relates to visual detection of air retention in small bore plastic syringes having volume capacities of one cc or less.

BACKGROUND OF THE INVENTION

A phenomenon frequently occurs in small bore hypodermic syringes having plastic syringe barrels, and especially those with a total medication capacity of one cc or less, of air retention in medication aspirated into the syringe barrel. It is believed this phenomenon, at least in part occurs due to the relationship of the surface tension and viscosity of the medication, the wetting coefficient of the plastic syringe walls, and the small internal bore diameter. Such air retention is identifiable as a bubble or bubbles which may form at any point or points along the length of the medication column aspirated into the syringe barrel. Retained bubbles of air require identification and evacuation prior to administration of the medication for two important reasons. Firstly, it is not healthy to inject air into tissues or the bloodstream. Secondly and perhaps even more importantly, the retained air displaces medication in the syringe barrel so the volumetric reading at the plunger piston incorrectly identifies the actual volume of medication in the syringe barrel. This leads the person administering the medication to incorrectly assume the dosage is correct. This may be fatal or at the least, result in ineffective or incomplete treatment.

Persons with normal vision, even medical professionals, find it difficult to detect the presence of bubbles in small syringe bores. The problem is greatly amplified for those persons who have poor eyesight. For example, diabetics, often visually impaired, are frequently required to inject themselves daily with medication. An unnoticed air bubble embedded in the contents of the diabetic's syringe may have a serious effect by displacing a volume of critically needed medication. Yet the most typical syringe used by diabetics is the plastic, small bore, disposable syringe; the very syringe which most frequently manifests the air retention problem.

Not only is it difficult to detect bubbles in small bore plastic syringes, it is also difficult to determine when and if detected bubbles have been properly evacuated from the syringe bore. Once identified, difficulty is often encountered in moving the bubbles to the syringe end for evacuation. The most common method used is tapping the barrel while holding the syringe with the needle pointing upwardly. This is done until observation reveals that the bubbles have collected in position to make the evacuation possible by plunger pressure.

Air bubble retention is particularly troublesome when using colorless medications such as are often used in small bore plastic hypodermic syringes. The interface between air and the colorless medication is especially difficult to detect. This is due to similarities of color of the air, liquid and optical properties of the plastic barrel walls.

The above problem has been recognized in prior U.S. patents but adequate solutions have been lacking.

For example, U.S. Pat. No. 4,178,071 to Asbell discloses a magnifying cylinder for insulin syringes. This device is comprised of an optical sleeve including a cylindrical internal bore for receiving the barrel of a syringe. Its purpose is to magnify the contents of the syringe to indicate a preset fluid level for medication within the syringe barrel. It is indicated in the specification that coloration could be provided along regions of the sleeve adjacent a slit on the back side of the sleeve for more readily visualizing the liquid level confined within the body of the syringe. It is indicated that "since insulin is usually colorless, a darkened background is useful but not necessary." While this device is serviceable to indicate a consistent dosage amount and does have the effect of magnifying the contents of the hypodermic syringe, it is a separate item from the syringe itself and does not specify the precise nature of the darkened background area whereby air bubbles in the medication could be easily visually detected.

Another magnifying attachment is shown in U.S. Pat. No. 2,586,581 to Tschischeck. This device incorporates a magnifying lens that attaches by means of semicircular clips to the barrel of a hypodermic syringe. The device amplifies the calibration indicia along the length of the barrel and the bottom surface of the syringe plunger, which is used for indicating volume within the syringe by its alignment with the calibrations along the barrel. This device represents a partial solution to the problem indicated above but, like the Asbell device, is separate from the hypodermic syringe itself and does not offer a definite visual detection arrangement for amplifying contrast between liquid and air within the syringe barrel.

The above two references are the only prior references known to deal even indirectly with the problem of air retention within small bore hypodermic syringes.

U.S. Pat. No. 3,690,312 to Leibinsohn discloses a venous pressure manometric device with a level magnifying arrangement. The level indicator is attached to the tubular "sight glass." A pattern is situated along the length of the indicator behind the sight glass. The pattern is shown as a "checkerboard" pattern that appears to occupy the full length of the tube. But unlike the drawing, the amplification of the pattern would occur only in the transverse plane and would enable detection of bubbles only through a visual comparison of the transverse widths of the darkened spaces. Various areas of the checkerboard pattern are transversely amplified by portions of the tube in which liquid is present and are diminished along potions of the tube where air is present. Since the width dimension of the strip described in the Leibinshohn patent is apparently at least equal to the external diameter of the sight tube, the pattern along the strip will constantly appear to occupy the full diameter of the tube regardless of whether air or liquid is present therein. The gas and liquid interface must therefore be distinguished by the reader's ability to visually distinguish between magnified and reduced transverse portions of the patterns through the sight tube. This arrangement is appropriate for persons having normal visual acuity, but to the visually impaired, the pattern may visually dissolve into a solid strip. Furthermore, the checkerboard pattern could confuse reading of calibrations on the opposite side of the tube.

U.S. Pat. No. 2,303,154 to Armstrong is concerned with the problem of detecting the air-liquid interface at the surface of a liquid column held in a conventional transparent volumetric laboratory glass tube. The meniscus at the top of the liquid column is made easier to locate by provision of a roughened strip along the length of the tube opposite to the volumetric indices. The strip width is stated to be about one third of the width of the instrument. It is important to note that the drawings show that the strip is magnified through the tube where air is present and is more magnified, or appears still larger where liquid is present. It is also stated that the strip may either be situated on the outside or inside surfaces of the tube wall, yet the visual images shown are the same in either instance. This incorrectly identifies the image as magnified when the strip is applied to the outward surface of the tube. Armstrong therefore would have lead one to consider that the visual difference between the two magnified images at the liquid-air interface, particularly if viewed through a small bore plastic syringe, would be relatively insignificant. Furthermore Armstrong in his solution to the particular problem of identifying the meniscus at the top of a fluid column, gives no consideration to the problem addressed in this application, of observing retained air within a plastic small bore hypodermic syringe. This is evident from the fact that the volume is from the interface of an air column and a liquid meniscus as taught in Armstrong, but a highly visible alignment between the syringe piston bottom and volume indicia on the syringe barrel.

The problem of correctly identifying the volume of a liquid column in a large bore, transparent hypodermic syringe is approached in U.S. Pat. No. 2,888,015 to Hunt. The solution, addressed specifically to the volume detection problem was to provide a multi-colored strip along the clear barrel of the syringe. The length of syringe barrel occupied by each color was to be associated with a particular volume of aspirated medication. No discussion whatever is made with regard to the air retention problem indicated above, or that the multi colored strip could be modified to provide an adequate solution to the quite different problem of observing retained air in plastic small bore syringes.

The present invention unlike that of Hunt and Armstrong, or any other known reference is specifically addressed to a solution of the particular problem of improving the visibility of air retained within an aspirated volume of liquid in small diameter (one cc or less) plastic hypodermic syringes.

This is done by providing a narrow reflective solid strip of a single color along an outward side of the small diameter plastic syringe barrel. The relationship between the tube diameter, the optical properties of the small bore plastic tube walls, and the strip width is such that the tube will have the appearance of containing a fluid of the particular strip color where liquid spans the tube bore. In areas of the tube containing air, the strip will appear narrow with clear spaces to either side extending to the interface between the air and liquid. The strip may be integral with the tube so no attachments are required. Full, brightly colored areas within the tube contrast with relatively clear areas and a reduced, diffused image of the same color dramatically emphasize the interface between gas and liquid within the tube, even to the visually impaired. This solution has no effect on the manner in which volumetric measurements are discerned. Volume measurements are still read in the usual way, by relating the syringe piston to volumetric indicia on the syringe barrel.

BRIEF DESCRIPTIONS OF THE DRAWINGS

A preferred embodiment of the invention is illustrated in the accompanying drawings, in which:

FIG. 1 is a front elevation view of a standard prior art small bore plastic hypodermic syringe;

FIG. 2 is a view of a small bore plastic syringe incorporating the present invention and with a conventional needle attached;

FIG. 3 is a rear view of a syringe barrel with a plunger but without a needle;

FIG. 4 is an enlarged sectional view taken substantially along line 4—4 in FIG. 2;

DETAILED DESCRIPTION OF THE PREFERRED EMBODIMENT

Figure 5:
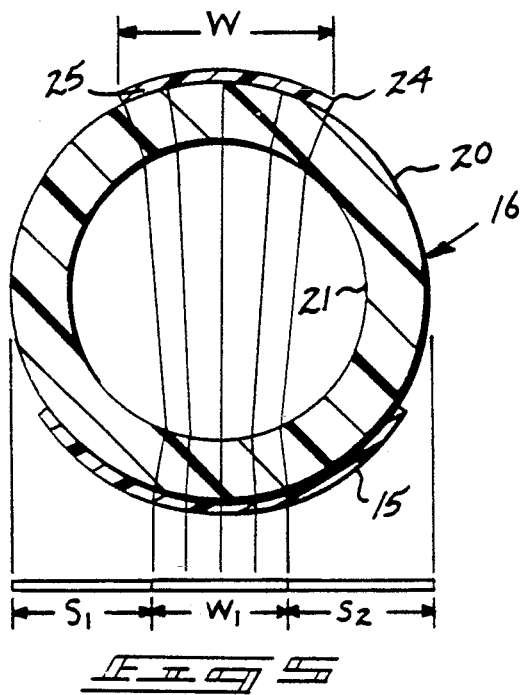
FIG. 5 is a diagrammatic view illustrating the reduced image size of a single color strip with properties described herein as it appears through the plastic barrel walls of the present syringe.

The following disclosure of the invention is submitted in compliance with the constitutional purpose of the Patent Laws "to promote the progress of science and useful arts" (Article 1, Section 8).

A small bore plastic syringe barrel exemplifying features of the present invention is shown in FIGS. 2-4. As a comparison, a standard prior art small bore hypodermic syringe 10 is shown in FIG. 1.

FIG. 1 graphically demonstrates the difficulty in observing the presence of an air bubble 14 through the conventional small bore plastic syringe barrel 13. The air bubble is indicated at 14 within a column of light transmissive liquid medication received within the syringe barrel 13. The small bore plastic syringe barrel 13 substantially diffuses light and, with clear liquid medication, the light passage through the syringe barrel renders it very difficult to visibly distinguish between the liquid and any retained air within the barrel. This is especially true for individuals, such as diabetics, who may have a vision impairment.

The surface represented by the plunger may thus indicate an incorrect volume within the syringe barrel due to presence of the bubble.

The present device exemplified in FIGS. 2-4, is a small bore plastic hypodermic syringe assembly including a tube body or barrel 16 having a volume capacity of approximately one cc or less. The tube body 16 is formed of light transmissive material such as the plastics typically utilized in construction of conventional small bore hypodermic syringe barrels.

In the preferred embodiment exemplified herein, the small bore tube body 16 extends from an open top end 17, adapted to receive a plunger 11. A plunger shaft 11a and a piston 11b are slidably received within the tube.

The tube also extends to a reduced bottom end 18 that may be tapered to releasably receive a conventional hypodermic needle 12 or may include a non-reusable needle. Calibration indicia 15 is provided along the length of the tubular body 16. It is important to note that the indicia 15 are standard hypodermic syringe markings of the type found on conventional syringes (FIG. 1). The volume of aspirated material in the present syringe is thus indicated in the usual manner, by the volumetric calibration indicia 15 which is presently aligned with the bottom surface of the piston 11b.

The small bore tube body 16 includes a substantially cylindrical outer axial wall 20. An inner wall 21 is preferably substantially coaxial with the outer wall 20. The inner wall 21 defines the axial bore, and the total volume capacity of the syringe (approximately one cc or less). Bores having larger volumetric capacity do not commonly manifest the air retention or visibility problems experienced with such small bore syringes.

The present tube body 16 includes a first front arcuate section 22 (FIG. 4). Section 22 includes the indicia 15. A second arcuate section 23 (FIG. 3) is substantially diametrically opposite the first section 22.

A very important feature of the present invention is an elongated colored strip 24 extending axially along the second arcuate section 23 of tube body 16. The selected strip 24 is integrated with the tube, extending axially along the tube from the reduced bottom end 18 (FIG. 3). The strip may be applied by painting, silk screening, printing or may otherwise be affixed to the outer tube wall 20. It may also be integrated with the outer tube wall 20 as by etching or by other appropriate coloration processes as the tube is formed.

The preferred material for the strip itself is selected for reflective and coloration properties contrasting with the color of the indicia 15 and the plunger piston 11b. The strip 24 is advantageously a single, solid reflective color that is consistent along the length of the tube body 16 and that cannot be confused with the indicia 15. Bright opaque red has been tested and has been found effective. Other highly reflective colors may also be effective, including current bright "day-glow", or other highly reflective, colors.

Thus, in manufacture of the present syringe, the plastic barrel, strip color and its reflective properties and width are all selected with the objective to produce a reflected image of the strip when viewed through the plastic walls of the tube from the first arcuate section that will (a) not visually interfere with or confuse standard volumetric reading of the syringe contents through use of the plunger piston bottom and volumetric indicia 15; (b) appear narrower than the internal diameter of the tube body and dull or diffused in appearance where air is present in the tube bore; and (c) appear bright and substantially as wide as the tube outer diameter where fluid is present in the axial bore.

A preferred strip 24 is selected to include longitudinal side edges 25. Edges 25 are advantageously parallel to one another and substantially parallel to the central longitudinal axis X (FIG. 4) of the tube body 16.

Another important feature is the selected chordal spacing or width dimension W (FIGS. 4–6) between the longitudinal side edges 25 of the strip 24 in relation to the overall outside diameter (O.D.) of the small bore plastic tube body 16.

The width W of the strip 24, (FIGS. 5,6) is selected in consideration of the syringe size, wall thickness and the plastic composition of the syringe body, to visually indicate a maximum disparity between areas occupied by liquid and areas occupied by air.

It is essential that a strip be selected having a width dimension W on the body 16 that is less than the overall O.D. of the outer tube wall 20. It is particularly advantageous with the small diameter plastic syringe (of one cc capacity or less) that the strip be approximately 50% of the O.D., or approximately 75% of the inside diameter (I.D.) of the inner wall 21.

Figure 6:
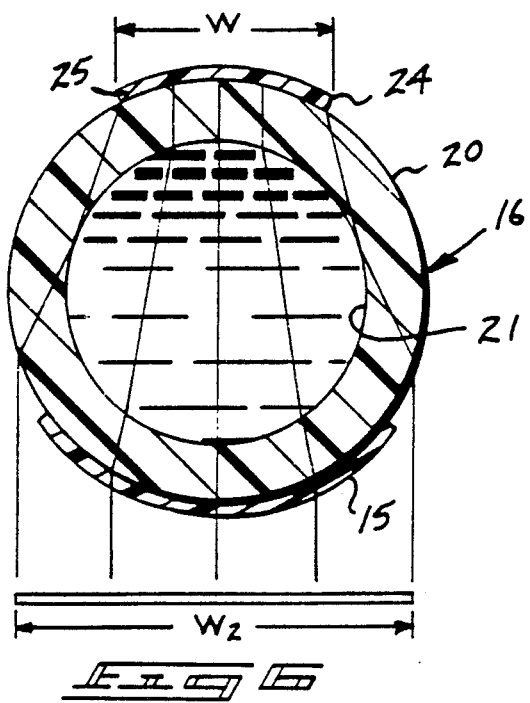
FIG. 6 is a diagrammatic view illustrating the magnified size of the strip as it appears through the plastic syringe barrel walls and through aspirated medication therein.

With a strip of the selected width W applied to a 1 cc or less plastic syringe body, the resulting image $W_2$ of the strip 24 will be bright and will appear to span the entire O.D. of the tube body where liquid is present. The enlarged image $W_2$ is shown by diagram in FIG. 6. The liquid aspirated into the tube body combines with the plastic syringe walls to form a cylindrical magnifier. The strip width W, at 50% of the tube body O.D. is magnified through the wetted plastic syringe walls and the column of aspirated material, so the image $W_2$ appears equal in width to the tube body O.D. The reflected rays are convergent (though for clarity only rays that are nearly parallel are shown in FIG. 6) due to the magnifying lens effect of the liquid and tube walls. The rays reflected from the reflective strip are thus concentrated and will produce a bright, sharp, and distinct magnified image.

Where air is present (FIG. 5) the strip image $W_1$ will appear through the small diameter plastic walls to be reduced in transverse dimension in relation to the actual strip width W. The image $W_1$ of the strip will also be diffused or duller and indistinct. The image $W_1$ is transversely reduced through the airspace within the body and the combination of curved lenses formed by the second or rear arcuate wall section 23, and the front first arcuate section 22. Clear uncolored spaces S1, S2 will also appear laterally adjacent to both sides of the narrow strip image $W_1$.

The dull, indistinct strip image $W_1$ is attributed to the number of non wetted plastic wall surfaces through which the reflected rays must pass where air is present. In an air space where there is no medication to wet the adjacent interior walls, the relatively dry plastic wall surfaces have a diffusing effect, dulling the image of the strip.

There is a stark, very visible contrast between areas where air is present in the tube body, and areas where liquid is present. Bubbles may be easily detected, even by the visually impaired simply by visually noting the narrowed, dull reflected image $W_1$ of the strip where it appears in sharp contrast in the presence of air, against the bright magnified image $W_2$ of the same color, fully occupying the tube body through liquid filled areas.

The selected strip width is important, especially considering the narrow or small diameter of the tube body 16 and the plastic tube walls.

For example, a strip substantially wider than the 50% O.D. will produce an image that appear to occupy the entire tube regardless of the presence of liquid or air within the tube bore. Less substantial demarcation between liquid and air will be visible.

A narrower strip (substantially less than 50% of the O.D.) will result in formation of a magnified image through liquid that will not "fill" the tube, and a reduced image through air that is not significantly different in width dimension than the magnified image.

Operation of the present device is similar regardless of the filling technique being used.

With the present hypodermic assembly, the user of multiple dose medication vials (not shown) first withdraws the plunger 11a, pulling air into the expansible chamber until the piston 11b end is adjacent the calibration indicia mark 15 indicating the amount of medication to be withdrawn. The strip 24 in this situation will appear uniformly dull and narrow and will not interfere with the users view of the plunger piston 11a and indicia 15.

Next, the syringe needle is inserted into the multiple dose vial and the plunger 11a is depressed to inject the previously aspirated volume of air into the vial. The injected air is compressed in the vial. This is done to avoid formation of a vacuum within the vial which eventually could build to the point where no medication could be removed.

The user may now fill the syringe barrel by releasing the plunger and allowing the pressurized air in the vial to force the medication into the syringe. An amount of the medication equal to the injected volume of air will be pushed into the syringe if the needle point is kept immersed in the medication. The strip in no way interferes with or confuses the volume identifying process, regardless of the volume or medication selected.

The user of medication in single use ampules, first scores and breaks the top off the ampule then inserts the needle into the medication and aspirates a quantity of medication. The syringe is then inverted with the needle pointing upwardly in order to identify, move and evacuate the air that invariably will be retained in the small bore of the syringe. After all air is evacuated, the needle is reinserted into the medication and the desired volume or more is aspirated as indicated by the piston bottom against the volume indices 15. Prior to injection the contents require re-examination for further retained air bubbles and final adjustment of accurate dosage, again using the piston bottom in alignment with the volume indices. When the prescribed dose is observed and the strip appears as a bright continuous solid coloration, filling the syringe between the piston bottom and the reduced bottom end 18, the user can feel confident that no air is displacing medication volume in the syringe. The medication can then be safely injected.

With either filling procedure indicated above, where air is present, the single coloration of the strip image 28 appears broken or discontinuous, dull and reduced in width where air is present. In sharp contrast to this image, bright, full syringe-width images are visible where the medication is present. Because the interface between the liquid surface and gas is dramatically emphasized, the user is able to easily detect the presence of air in the syringe and take the necessary steps to remove it.

The hypodermic assembly has additional benefits to the user when more than one medication is to be used, as where two forms of insulin are to be used in a single injection.

To "mix" medications, the user withdraws a first amount of medication from a first bottle in the manner discussed above. Holding the syringe with the needle pointed upwardly, the user then withdraws the plunger further, until the top surface of the first medication reaches the volume calibration indicated for the second amount of medication. This is readily accomplished with the present arrangement since the volume of the first insulin medication will amplify the strip image so the top surface of the first medication will appear to occupy the full diameter of the expansible syringe chamber and the surface of the medication will be easily detected against the dull narrow strip image where there is air in the chamber. Next, the user inserts the needle into the second insulin bottle and presses the plunger to inject the second air volume into that bottle. Once this is accomplished, the user then again withdraws the plunger, pulling the second volume of insulin into the syringe, along with the earlier withdrawn first insulin medication. The plunger is withdrawn until the total volume required is indicated adjacent to the piston plunger bottom. Again, any air bubbles will be easily detected due to presence of the strip and the optical qualities described above.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the Doctrine of Equivalents.

I claim:

1. A method of detecting air bubbles in a hypodermic syringe having a light transmissive tubular body with an internal bore of a prescribed diameter extending between an open end and a reduced end, an elongated plunger with a piston at an end thereof slidably received in the bore, volume calibration indicia along the body, and an elongated strip of a single solid color extending longitudinally along the tubular body independently of the volume calibration indicia and having a chordal width dimension less than the prescribed diameter; comprising the steps of:

drawing a light transmissive liquid into the syringe bore by moving the plunger within the bore from the reduced end toward the open end until the plunger piston aligns visually with a prescribed volume calibration indicia; and viewing the strip of solid color through the tubular body along the full length thereof between the plunger piston and reduced end to note that the solid strip of color appears to fill substantially the entire bore as a single solid color occupying the entire bore diameter thereby indicating presence of only liquid in the bore between the piston and reduced end of the tubular body, or that a portion of the strip between the piston and reduced end appears substantially narrower than the bore diameter thereby indicating presence of a bubble within the bore.

* * * * *